(12) United States Patent
Chien et al.

(10) Patent No.: US 7,670,559 B2
(45) Date of Patent: *Mar. 2, 2010

(54) MICROFLUIDIC SYSTEMS WITH ENHANCED DETECTION SYSTEMS

(75) Inventors: Ring-Ling Chien, San Jose, CA (US); Jeffrey A. Wolk, Half Moon Bay, CA (US); Michael Spaid, Sunnyvale, CA (US); Richard J. McReynolds, San Jose, CA (US)

(73) Assignee: Caliper Life Sciences, Inc., Alameda, CA (US)

( * ) Notice: Subject to any disclaimer, the term of this patent is extended or adjusted under 35 U.S.C. 154(b) by 1728 days.

This patent is subject to a terminal disclaimer.

(21) Appl. No.: 10/225,454

(22) Filed: Aug. 19, 2002

(65) Prior Publication Data

US 2003/0036206 A1    Feb. 20, 2003

Related U.S. Application Data

(63) Continuation-in-part of application No. 10/076,136, filed on Feb. 14, 2002, now abandoned.

(60) Provisional application No. 60/269,174, filed on Feb. 15, 2001.

(51) Int. Cl.
*G01N 33/48* (2006.01)
(52) U.S. Cl. .................... 422/100; 422/102
(58) Field of Classification Search ............ 422/56, 422/58, 61, 99–104
See application file for complete search history.

(56) References Cited

U.S. PATENT DOCUMENTS

| | | | |
|---|---|---|---|
| 4,330,206 A | 5/1982 | Gausmann et al. | |
| 4,390,403 A | 6/1983 | Batchelder | |
| 4,908,112 A | 3/1990 | Pace | |
| 5,126,022 A | 6/1992 | Soane et al. | |
| 5,498,392 A | 3/1996 | Wilding et al. | |
| 5,571,410 A | 11/1996 | Swedberg et al. | |
| 5,585,069 A | 12/1996 | Zanzucchi et al. | |
| 5,593,838 A | 1/1997 | Zanzucchi et al. | |

(Continued)

FOREIGN PATENT DOCUMENTS

GB    1407247    9/1975

(Continued)

OTHER PUBLICATIONS

Cohen, C.B. et al., "A Microchip-Based Enzyme Assay for Protein Kinase A," *Analytical Biochemistry* (1999) 273:89-97.

(Continued)

*Primary Examiner*—Lyle A Alexander
(74) *Attorney, Agent, or Firm*—Cardinal Law Group

(57) ABSTRACT

Microfluidic devices and systems having enhanced detection sensitivity, particularly for use in non-fluorogenic detection methods, e.g., absorbance. The systems typically employ planar microfluidic devices that include one or more channel networks that are parallel to the major plane of the device, e.g., the predominant plane of the planar structure, and a detection channel segment that is substantially orthogonal to that plane. The detection system is directed along the length of the detection channel segment using a detection orientation that is consistent with conventional microfluidic systems.

5 Claims, 10 Drawing Sheets

U.S. PATENT DOCUMENTS

| | | | |
|---|---|---|---|
| 5,599,503 A | 2/1997 | Manz et al. | |
| 5,603,351 A | 2/1997 | Cherukuri et al. | |
| 5,635,358 A | 6/1997 | Wilding et al. | |
| 5,637,469 A | 6/1997 | Wilding et al. | |
| 5,699,157 A | 12/1997 | Parce | |
| 5,716,852 A | 2/1998 | Yager et al. | |
| 5,750,015 A | 5/1998 | Soane et al. | |
| 5,757,482 A | 5/1998 | Fuchs et al. | |
| 5,800,690 A | 9/1998 | Chow et al. | |
| 5,842,106 A * | 11/1998 | Thaler et al. .................. | 419/8 |
| 5,858,187 A | 1/1999 | Ramsey et al. | |
| 5,858,195 A | 1/1999 | Ramsey | |
| 5,869,004 A | 2/1999 | Parce et al. | |
| 5,876,675 A | 3/1999 | Kennedy | |
| 5,880,071 A | 3/1999 | Parce et al. | |
| 5,882,465 A | 3/1999 | McReynolds | |
| 5,885,470 A | 3/1999 | Parce et al. | |
| 5,928,880 A | 7/1999 | Wilding et al. | |
| 5,932,100 A | 8/1999 | Yager et al. | |
| 5,942,443 A | 8/1999 | Parce et al. | |
| 5,948,227 A | 9/1999 | Dubrow | |
| 5,955,028 A | 9/1999 | Chow | |
| 5,958,694 A | 9/1999 | Nikiforov | |
| 5,959,291 A | 9/1999 | Jensen | |
| 5,965,410 A | 10/1999 | Chow et al. | |
| 5,976,336 A | 11/1999 | Dubrow et al. | |
| 5,989,402 A | 11/1999 | Chow et al. | |
| 6,001,229 A | 12/1999 | Ramsey | |
| 6,001,231 A | 12/1999 | Kopf-Sill | |
| 6,012,902 A | 1/2000 | Parce | |
| 6,042,709 A | 3/2000 | Parce et al. | |
| 6,046,056 A | 4/2000 | Parce et al. | |
| 6,062,261 A | 5/2000 | Jacobson et al. | |
| 6,074,725 A | 6/2000 | Kennedy | |
| 6,100,541 A | 8/2000 | Nagle et al. | |
| 6,120,666 A | 9/2000 | Jacobson et al. | |
| 6,221,226 B1 | 4/2001 | Kopf-Sill | |
| 6,224,830 B1 | 5/2001 | Harrison et al. | |
| 6,235,471 B1 | 5/2001 | Knapp et al. | |
| 6,280,589 B1 | 8/2001 | Manz et al. | |
| 6,319,472 B1 | 11/2001 | Ackley et al. | |

FOREIGN PATENT DOCUMENTS

| | | |
|---|---|---|
| WO | WO-9604547 | 2/1996 |
| WO | WO-9702357 | 1/1997 |
| WO | WO-9944217 | 9/1999 |
| WO | WO-0120309 | 3/2001 |

OTHER PUBLICATIONS

Daridon, A. et al., "Chemical Sensing Using an Integrated Microfluidic System Based on the Berthelot Reaction," *Sensors and Actuators B* (2001) 76:235-243.

Dasgupta, P.K. et al., "Electroosmosis: A Reliable Fluid Propulsion System for Flow Injection Analysis," *Anal. Chem.* (1994) 66:1792-1798.

Denninger, M. et al., "Absorbance Detection in Microsystems: Microcuvette and Waveguide Approach," Eurosensors XIV (2000) 825-827.

Effenhauser, C.S. et al., "Glass Chips for High-Speed Capillary Electrophoresis Separations with Submicrometer Plate Heights," *Anal. Chem.* (1993) 65: 2637-2642.

Effenhauser, C.S. et al., "High Speed Separation of Anitsense Oligonucleotid on a Micromachined Capillary Electrophoresis Device," *Anal. Chem.* (1994) 66: 2949-2953.

Effenhauser, C.S. et al., "Integrated Capillary Electrophoresis on Flexible Silicone Microdevices: Analysis of DNA Restriction Fragments and Detection of Single DNA Molecules on Microchips," *Anal. Chem.* (1997) 69: 3451-3457.

Fan, Z.H. et al., "Micromachining of Capillary Electrophoresis Injectors and Separators on Glass Chips and Evaluation of Flow at Capillary Intersections," *Anal. Chem.* (1994) 66: 177-184.

Fister, J.C. III et al., "Counting Single Chromophore Molecles for Ultrasensitive Analysis and Separations on Microchip Devices," *Anal. Chem.* (1998) 70: 431-437.

Hadd, A.G. et al., "Microfluidic Assays of Acetylcholinesterase," *Anal. Chem.* (1999) 71: 5206-5212.

Harrison, J. et al., "Capillary Electrophoresis and Sample Injection Systems Integrated on a Planar Glass Chip," *Anal. Chem.* (1992) 64: 1926-1932.

Harrison, J. et al., "Towards Miniaturized Electrophoresis and Chemical Analysis Systems on Silicon: An Alternative to Chemical Sensors*," *Sensors and Actuators B* (1993) 10: 107-116.

Harrison, J. et al., "Micromachining a Miniaturized Capillary Electrophoresis-Based Chemical Analysis System on a Chip," *Science* (1993) 261: 895-897.

Harrison, D.J. et al., "Integrated Electrophoresis Systems for Biochemical Analyses," *Solid-State Sensor and Actuator Workshop* (1994) 21-24.

Jacobson, S.C. et al., "Effects of Injection Schemes and Column Geometry on the Performance of Microchip Electrophoresis Devices," *Anal. Chem.* (1994) 66:1107-1113.

Jacobson, S.C. et al., "High-Speed Separations on a Microchip," *Anal. Chem.* (1994) 66: 1114-1118.

Jacobson, S.C. et al., "Open Channel Electrochromatography on a Microchip," *Anal. Chem.* (1994) 66: 2369-2373.

Jacobson, S.C. et al., "Precolumn Reactions with Electrophoretic Analysis Integrated on a Microchip," *Anal. Chem.* (1994) 66: 4127-4132.

Jacobson, S.C. et al., "Microchip Electrophoresis with Sample Stacking," *Electrophoresis* (1995) 16: 481-486.

Jacobson, S.C. et al., "Fused Quartz Substrates for Microchip Electrophoresis," *Anal. Chem.* (1995) 67: 2059-2063.

Jacobson, S.C. et al., "Integrated Microdevice for DNA Restriction Fragment Analysis," *Anal. Chem.* (1996) 68: 720-723.

Jacobson, S.C. et al., "Electrokinetic Focusing in Microfabricated Channel Structures," *Anal. Chem.* (1997) 69: 3212-3217.

Jacobson, S.C. et al., "Microfluidic Devices for Electrokinetically Driven Parallel and Serial Mixing," *Anal. Chem.* (1999) 71: 4455-4459.

Liang, Z. et al., "Microfabrication of a Planar Absorbance and Fluorescence Cell for Integrated Capillary Electrophoresis Devices," *Anal. Chem.* (1996) 68:1040-1046.

Manz, A. et al., "Miniaturized Total Chemical Analysis Systems: a Novel Concept for Chemical Sensing," *Sensors and Actuators* (1990) B1: 244-248.

Manz, A. et al., "Micromachining of Monocrystalline Silicon and Glass for Chemical Analysis Systems," *Trends in Analytical Chemistry* (1991) 10:144-149.

Manz, A. et al., "Planar Chips Technology for Miniaturization and Integration of Separation Techniques into Monitoring Systems," *Journal of Chromatography* (1992) 593:253-258.

Manz, A. et al., "Electroosmotic Pumping and Electrophoretic Separations for Miniaturized Chemical Analysis Systems," *J. Micromach. Microeng.* (1994) 4: 257-265.

Manz, A. et al., "Parallel Capillaries for High Throughput in Electrophoretic Separations and Electroosmotic Drug Discovery Systems," International Conference on Solid-State Sensors and Actuators (1997) 915-918.

McCormick, R.M. et al., "Microchannel Electrophoretic Separations of DNA in Injection-Molded Plastic Substrates," *Anal. Chem.* (1997) 69: 2626-2630.

Moore, A.W. et al., "Microchip Separations of Neutral Species via Micellar Electrokinetic Capillary Chromatography," *Anal. Chem.* (1995) 67: 4184-4189.

Ramsey, J.M. et al., "Microfabricated Chemical Measurment Systems," *Nature Medicine* (1995) 1:1093-1096.

Salimi-Moosavi, H. et al., "Biology Lab-on-a-Chip for Drug Screening," Solid-State Sensor and Actuator Workshop (1998) 350-353.

Seiler, K. et al., "Planar Glass Chips for Capillary Electrophoresis: Repetitive Sample Injection, Quantitation, and Separation Efficiency," *Anal. Chem.* (1993) 65:1481-1488.

Seiler, K. et al., "Electroosmotic Pumping and Valveless Control of Fluid Flow within a Manifold of Capillaries on a Glass Chip," *Anal. Chem.* (1994) 66:3485-3491.

Sundberg, S., "High-Throughput and Ultra-High-Throughput Screening: Solution-and Cell-Based Approaches," *Analytical Biotechnology* (2000) 47-53.

Ueda, M. et al., "Imaging of a Band for DNA Fragment Migrating in Microchannel on Integrated Microchip," *Materials Science and Engineering C* (2000) 12:33-36.

Wang, C. et al., "Integration of Immobilized Trypsin Bead Beds for Protein Degestion within a Microfluidic Chip Incorporating Capillary Electrophoresis Separations and an Electrospray Mass Spectrometry Interface," *Rapid Commin. Mass Spectrom.* (2000) 14:1377-2383.

Woolley, A.T. et al., "Ultra-High-Speed DNA Fragment Separations Using Microfabricated Capillary Array Electrophoresis Chips," *Proc. Natl. Acad. Sci. USA* (1994) 91:11348-11352.

Woolley, A.T. et al., "Functional Integration of PCR Amplification and Capillary Electrophoresis in a Microfabricated DNA Analysis Device," Anal. Chem. (1996) 68: 4081-4086.

Woolley, A.T. et al., "High-Speed DNA Genotyping Using Microfabricated Capillary Array Electrophoresis Chips," *Anal. Chem.* (1997) 69:2181-2186.

Woolley, A.T. et al., "Capillary Electrophoresis Chips with Integrated Electrochemical Detection," *Anal. Chem.* (1998) 70: 684-688.

Zhang, B. et al., "Microfabricated Devices for Capillary Electrophoresis-Electrospray Mass Spectrometry," *Anal. Chem.* (1999) 71:3258-3264.

* cited by examiner

MICROFLUIDIC SYSTEMS WITH ENHANCED DETECTION SYSTEMS

CROSS-REFERENCE TO RELATED APPLICATIONS

This application is a continuation in part of U.S. Ser. No. 10/076,136, filed Feb. 14, 2002, which claims priority to U.S. Ser. No. 60/269,174, filed Feb. 15, 2001, each of which is incorporated herein in its entirety for all purposes.

BACKGROUND OF THE INVENTION

Microfluidic devices and systems have been developed that give researchers substantial advantages in terms of the miniaturization, automation and integration of a large number of different types of analytical operations. For example, continuous flow microfluidic devices have been developed that perform serial assays on extremely large numbers of different chemical compounds, e.g., for use in high-throughput pharmaceutical screening operations (see, e.g., U.S. Pat. Nos. 5,942,443 and 6,046,056). Other microfluidic devices have been developed that perform rapid molecular separations on a number of different samples in relatively short time frames (see, U.S. Pat. No. 5,976,336). All of these devices and systems share the ability to rapidly perform a wide range of different analytical operations.

Planar microfluidic analytical systems have a large number of advantages in terms of speed, accuracy and automatability. Despite these advantages, these planar channel systems suffer from a problem that is common to conventional capillary analytical systems. In particular, capillary systems, because of their extremely small volumes, can suffer from severely restricted sensitivity due to the simple lack of detectable amounts of material. For example, detection of materials in capillary or planar channel systems is typically accomplished by detecting signals from the channels in a direction orthogonal to the plane of the capillary or channel. This results in only the small amount of material that is present at the detection spot being subjected to the detection operation at any given time. In many cases, this deficiency is overcome using labeling techniques that have higher quantum yields of detectability, e.g., through fluorescence, chemiluminescence, radioactivity, etc. Of course, the use of these detection schemes requires the presence of a natural or added label that is detectable by these schemes. In many interesting analytical reactions, such labels are not readily available, or will themselves have a deleterious effect on the reaction to be analyzed.

As a result of reduced sensitivity, it previously has been difficult to utilize a number of different detection strategies in microfluidic systems, e.g., those strategies that have lower quantum detection yields or rely for sensitivity on the detection path length. For example, detection of low concentrations of analytes has been difficult in such systems, as has detection based upon non-fluorescent optical means, e.g., detection based upon absorbance.

Accordingly, it would be highly desirable to provide microfluidic systems that overcome these previously encountered shortcomings of microfluidic technology, namely, systems that have enhanced sensitivity for optical detection. The present invention meets these and a variety of other needs.

SUMMARY OF THE INVENTION

The present invention generally provides systems and methods for performing analytical operations in microscale fluidic channels, wherein those systems and methods have enhanced sensitivity for optical detection.

In a first aspect, the present invention provides systems of detecting optically detectable materials in microscale channels. The systems include at least a first detection channel segment and an optical detector that is oriented to direct a detection path through the detection channel segment at an angle that is non-orthogonal to the longitudinal axis of the detection channel segment. A variety of different non-orthogonal angles are optionally employed for the detection path relative to the longitudinal axis. In certain preferred aspects, the detection path is through the channel segment and substantially parallel to the longitudinal axis of the detection channel segment, e.g., the angle between the detection path and the longitudinal axis is approximately 0°.

In a second aspect, the invention provides a method of reducing stagnant fluid flow within a sample channel segment of a microfluidic device, comprising providing a microfluidic device having a sample channel segment having first and second ends and at least a first and second channel segment fluidly coupled to said sample channel segment at said first end and at least third and fourth channel segments fluidly coupled to the sample channel segment at the second end, wherein the first, second, third and fourth channel segments are orthogonal to the sample channel segment; and flowing a fluid simultaneously from said first and second channel segment into said sample channel segment and out through said third and fourth channel segments. The method may further comprise providing at least fifth and sixth channel segments which are fluidly coupled to said first end of the sample channel segment, and flowing a fluid simultaneously from the first, second, fifth and sixth channel segments into the sample channel segment. For example, in one preferred aspect, the first, second, fifth and sixth channel segments form a channel network having a figure 8 configuration. At least one of the pair of first and second channel segments or the pair of second and third channel segments can be provided with a channel portion having a wider cross-sectional diameter than a cross-sectional diameter of the sample channel segment.

In a related aspect of the invention, a microfluidic device is disclosed which comprises a body structure comprising at least first, second and third planar substrate layers mated together; a first channel network disposed between the first and second substrate layers, the first channel network comprising at least first and second channel segments; a second channel network disposed between the second and third substrate layers; and at least a first channel providing fluid communication between the first and second channel networks, the first and second channel segments of the first channel network being fluidly coupled to said first channel whereby at least two fluid streams may be simultaneously flowed into the first channel from the first channel network. The at least two fluid streams flowing into the first channel help to reduce stagnant fluid flow within the first channel. The first channel network may further comprise at least third and fourth channel segments which are also in fluid communication with the first channel such that the first channel network has a figure 8 configuration.

DETAILED DESCRIPTION OF THE INVENTION

The present invention is generally directed to microfluidic systems that have enhanced optical detection capabilities over previously described microfluidic systems. In particular, the present invention provides microfluidic devices that include channel segments that are oriented to provide optical detection through a sample material via an increased detection path length and/or sample material volume as compared to systems using conventional detection schemes where the detector is positioned to detect orthogonally to the detection channel segment. For example, in one embodiment, the detection path is along the length and parallel to the detection channel segment as opposed to in a direction orthogonal to the channel segment. By orienting the detection channel so as to direct and/or receive light in a direction parallel to the channel, e.g., the detection path is along the longitudinal axis of the detection channel segment, one can increase the sensitivity of the detection system. For example, in absorbance-based detection systems signal level, and thus sensitivity, is proportional to the detection path length. Therefore, by increasing detection path length, one increases the signal level and sensitivity of the assay.

In addition to providing for detection along the longitudinal axis of the detection channel segment, the systems of the present invention orient the detection channel segment orthogonally to the primary plane of the body structure of the microfluidic device. By doing this, one can detect along the length of the detection channel segment using conventional detection systems/device orientations, e.g., that direct a detector at an upper or lower surface of a microfluidic device, rather than at a side or edge of such a device. This provides the additional advantage of not requiring the incorporation of light guides within the body structure of the microfluidic device to ensure optimal transmission of signal through the body, as would be required in an edge directed detector. See, e.g., Liang et al. Anal. Chem. 1996, 68(6):1040-1046. Thus, the present invention permits enhanced detection, while using conventional systems and without requiring complex optical elements within the body of a microfluidic device.

Figure 1A:
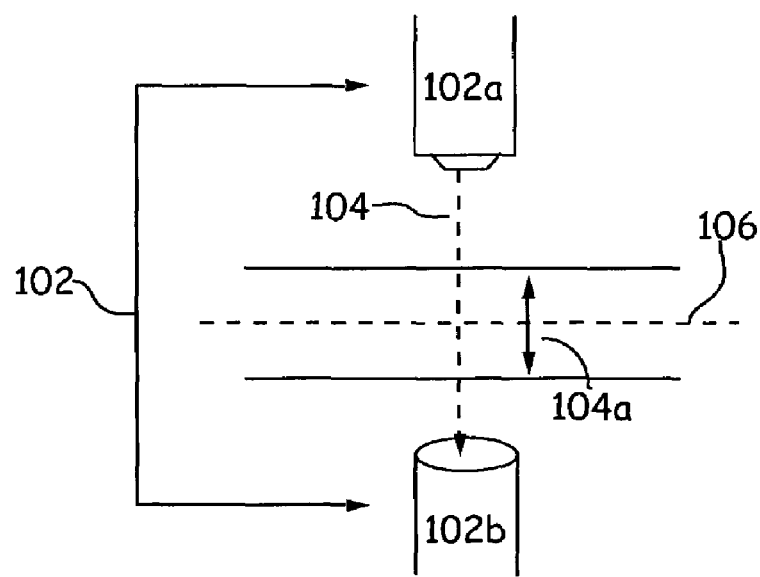
FIGS. 1A and 1B schematically illustrate the relative orientation of the detection channel and detection system of a conventional microfluidic system as compared with a microfluidic system of the present invention, employing a detection path that is along the length of the detection channel segment.
Figure 1B:
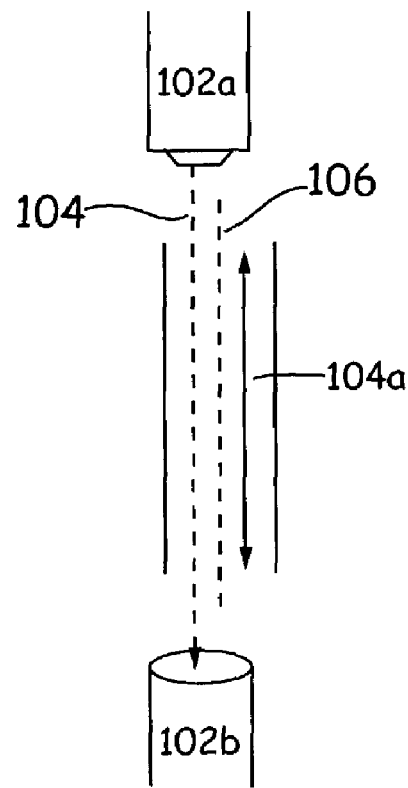

This system orientation is schematically illustrated in FIGS. 1A and 1B. In particular, the systems of the present invention include a channel segment 100 containing a volume of fluid having a concentration of a first detectable component disposed therein. Also included is a detection system 102 (shown as including light source 102a and detector 102b) disposed in sensory communication with the channel segment 100 such that the detection path 104, e.g., the path from which the detector detects the detectable signal, passes through the detection channel segment. As shown, the detection system is an absorbance detector that primarily comprises a light source 102a and a light detector 102b for detecting the amount of light transmitted through the sample material. As used herein, the phrase "in sensory communication with a channel segment" refers to the positioning of a detection element, e.g., an optical detector, relative to the channel segment, such that the detector can detect a detectable signal from the channel segment, or a material disposed in the channel segment. In the case of optical detectors, sensory communication denotes the ability of the detector to receive optical signals from a material disposed within the channel segment, e.g., sample materials and the like.

In conventional microfluidic systems, e.g., as shown in FIG. 1A, the detection path is orthogonal to the longitudinal axis 106 of the channel segment. As a result, the length of that portion of the detection path (represented as arrow 104a) that passes through the channel segment is substantially equal to the cross sectional dimension of the channel segment, e.g., its depth, width, or in the case of cylindrical channels, its diameter. This yields a relatively short detection path length that is defined by the cross sectional dimension of the detection channel (for non-absorbance based detection systems, this also results in a smaller amount of material from which to detect a signal). In cases where the detectable material is at relatively low concentrations, there may not be sufficient material present in the detection path to reach the limit of detection of the detection system used. For example, the detection path may be sufficiently short that it does not absorb any measurable amounts of light.

In accordance with the present invention, the detection channel segment is oriented relative to the detector such that the detection path length through the channel segment is longer than simply the cross-sectional dimension, e.g., the depth, width or diameter. FIG. 1B illustrates an example of a system according to the present invention where the detection system 102 is oriented such that the detection path 104 passes substantially through the length of the detection channel segment 100, and is parallel to the longitudinal axis 106 of that channel segment. In this case, the portion of the detection path 104 (the portion is illustrated as arrow 104a), is substantially longer than in the case of FIG. 1A and is limited primarily by the length of the channel segment 100.

Figure 2A:
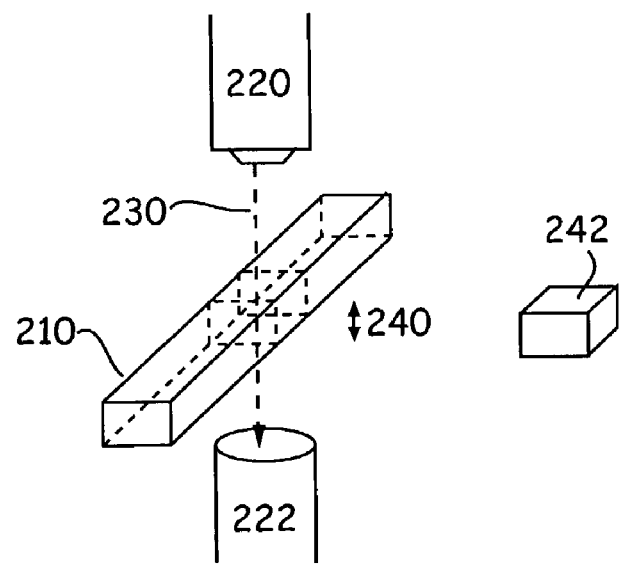
FIGS. 2A and 2B schematically illustrate a comparison of a conventional system and a detection system used in accordance with the present invention, illustrating advantages of the present system.
Figure 2B:
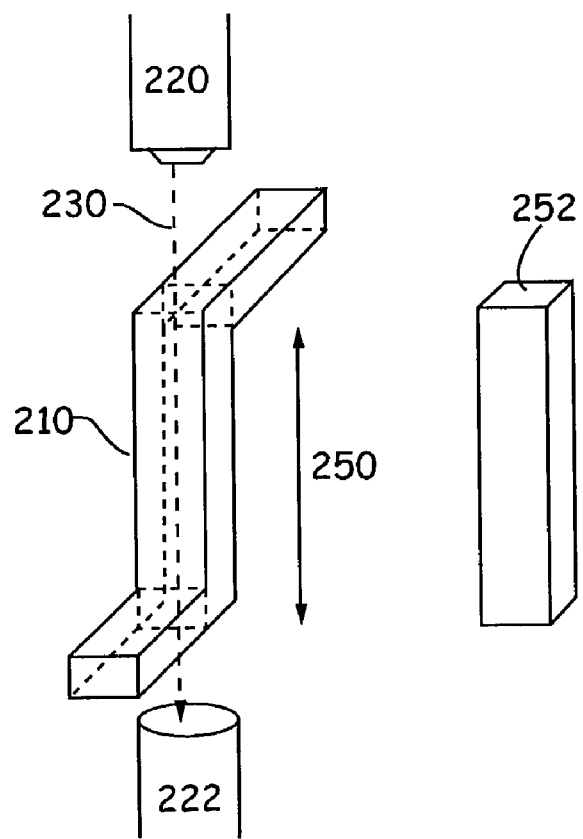

The present invention is further schematically illustrated in FIGS. 2A and 2B. FIG. 2A illustrates a conventional system incorporating a microscale channel 210, e.g., a capillary lumen or channel in a planar microfluidic device, in which an optical detection system (that is shown as including light source 220 and transmittance detector 222) is directed at the channel in a direction orthogonal to the plane of the channel. This orientation is typical in microfluidic systems where channels are in the main plane of the planar body of the microfluidic device. This results from the channels being defined at the interface of two or more laminated planar substrate layers. This orientation results in a relatively short detection path length 240. This orientation also results in a much smaller quantity of material 242 from which detection is sought. This is of particular concern in, e.g., fluorescence based detection systems, where sensitivity is obtained by increasing the amount of emitted light from the sample.

Where the concentration of the material to be detected is sufficiently high in the sample material such that the detection path length 240 through volume 242 contains a detectable amount of material, then detection sensitivity is not a concern, and the detection path length can be relatively short. However, in many cases where the concentration of material in the detection volume 242 is sufficiently low, detection path length 240 will be too short to provide for adequate detection, e.g., the detection path will be too short to absorb any measurable amounts of light.

FIG. 2B illustrates the configuration in accordance with the present invention that increases the detection path length and/or the volume of material that is subject to detection and thereby increases the sensitivity of that detection. In particular, in this system configuration, the detection system 220/222 is oriented relative to the detection channel 210 such that the detection path is in a direction that is parallel to and through the plane of channel segment 210, such that the detector is capable of detecting material through a much longer detection path length 250, e.g., through the length of material volume 252, also shown separate from the channel for illustration purposes (and thereby being capable of detecting much more material, even though such material might be at the same concentration as in FIG. 2A). One can readily adjust the detection path length, as well as the amount of material that is detected, by varying the length of the detection channel segment 210. A primary feature of this particular embodiment of the invention is that the detector directs and/or receives optical signals in the same plane as, e.g., parallel to and along the axis of the detection channel segment.

Although described primarily in terms of absorbance detection that is proportional to detection path length, it will be appreciated that the present invention is also useful in other types of detection, e.g., fluorescence based detection. In such instances, the signal is proportional to the amount of labeled material that is subject to detection. Assuming a uniform concentration of such material in a sample, then the amount of material subject to detection is proportional to the volume of material subject to detection. As can be seen from FIGS. 2A and 2B, the present invention shown in FIG. 2B provides for larger detection volume 252 as compared to the detection volume 242 of conventional systems as shown in FIG. 2A. In the cases of fluorescence based detection, a standard fluorescence detection system is employed, e.g., as in an Agilent 2100 Bioanalyzer system.

In accordance with the present invention, the detection path length typically is a function of thickness of the center layer of a layered microfluidic device. Specifically, the detection channel is provided as a via through the center substrate, e.g., as described in greater detail below. As such, the length of that channel is substantially defined by the thickness of that substrate. In the case of glass or quartz substrates, the thickness can vary from about 0.2 mm to 10 mm or even greater, depending upon the needs of the particular application to which the device is to be put. Other substrates can be used that are substantially thinner, including metal or polymer films, silicon substrates, etc. Typically, substrates are selected that are thinner than about 1 mm. In general, the detection path length is from about 10 µm to about 1 mm, and is preferably from about 50 µm to about 500 µm in length, and more preferably from about 100 to about 250 µm in length. Further, it is generally preferred that the cross-sectional area of the detection channel segment be comparable to the cross sectional area of at least the channel that feeds material into that detection channel segment, and more preferably, all channel segments that are fluidly connected to the detection channel segment. As used herein, the phrase "fluidly connected," "fluid communication" or derivations of these terms refer to the communication between two or more channels, chambers or other structures capable of containing fluid, whereby fluid would be able to freely pass, e.g., no mechanical barriers. Such fluid communication may be direct, e.g., a first channel intersecting a second channel, or it may be indirect, e.g., a first and second channel communicating via one or more additional channels or channel segments.

Figure 7A:
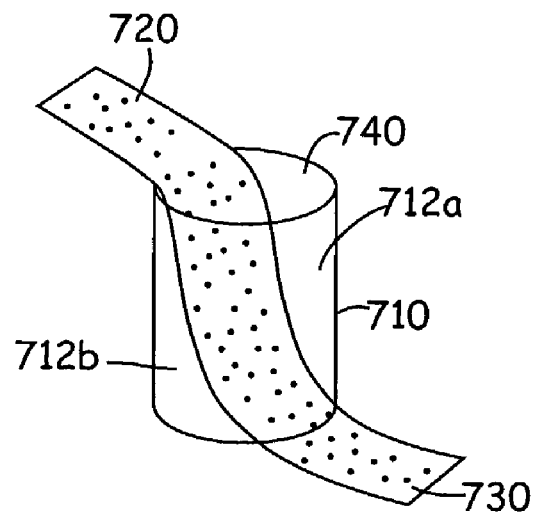
FIG. 7 panels A and B illustrates the improvement of fluid flow in a narrow channel region wherein fluid is flowed into the channel region via two inlets and out of the channel region via two outlets.
Figure 7B:
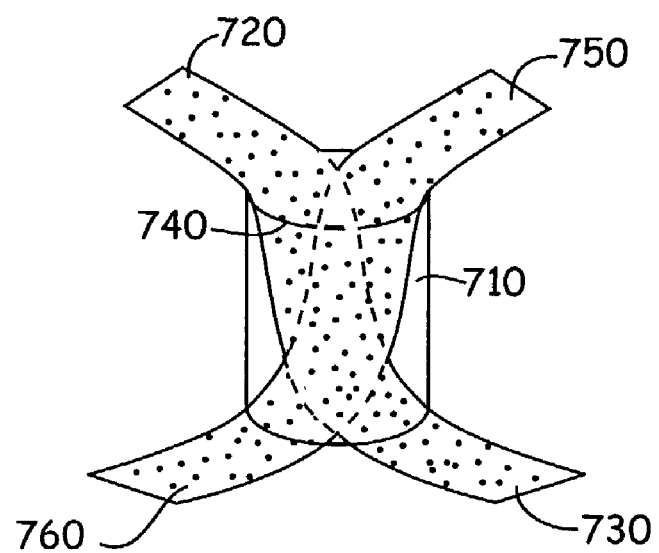
Figure 9:
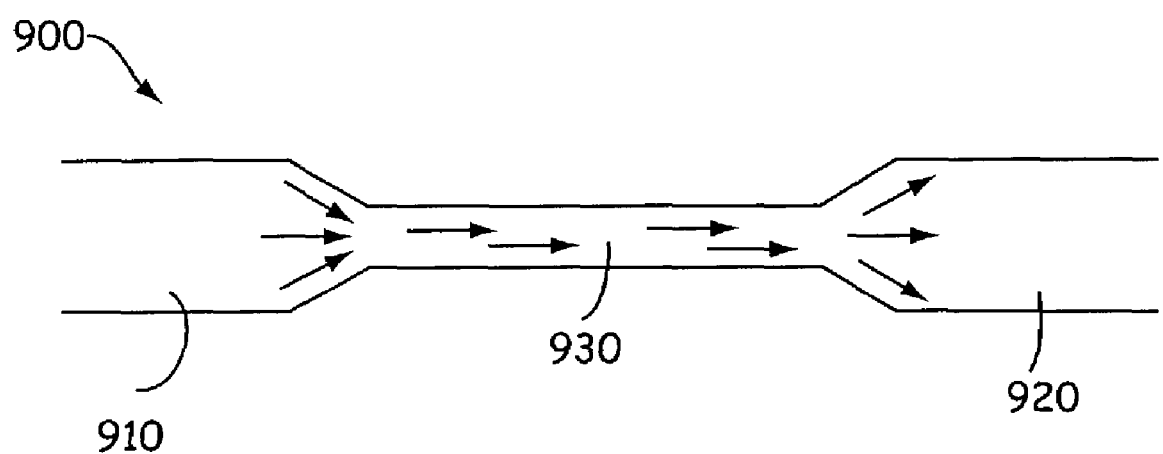
FIG. 9 illustrates an embodiment of a channel design of a device of the invention for improved rinsing of a narrow channel region.

By closely matching cross-sectional areas of the various channels, one substantially reduces the likelihood of dead zones within the junction between the channels of the device, e.g., the first channel and the detection channel, that can result in convective flow patterns that can disrupt the cohesiveness of discrete plugs of fluid sample materials as well as result in non-uniform fluid flow within the channels resulting in carryover between samples and contamination. For example, in devices with a through-hole or detection channel that connects two channel networks situated in different substrate layers with only one inlet and one outlet, "dead" pockets in the flow field can lead to an inefficient rinsing of the through-hole or detection channel. The stagnant flow pockets are more significant for channels having a cross-section larger than the inlet and the outlet. An illustration of this problem is shown in FIG. 7, panel A depicting the flow pattern for a sample plug to pass through a channel 710 connected by a single inlet and outlet channels, 720 and 730 respectively. As shown, the stagnant areas 712a and 712b of the fluid flow in this case are located in the detection channel opposite to the inlet and outlet channels. The stagnant area in the flow can result in a non-uniform sample concentration profile through the channel and thereby be detrimental to the assay or analysis being performed in the device. These problems are solved by the devices of the present invention by providing devices with channel structures suitable for facilitating improved fluid flow patterns through the channels. In particular, the detection channel segment typically comprises a cross sectional area that is from about 0.1 to about 5 times the cross-sectional area of at least the channel that feeds the detection channel. Preferably, the cross-sectional area of the detection channel segment is from about 0.5 to about 2 times the cross-sectional area of the channel feeding the detection channel. In still more preferred aspects, the cross sectional area is within about 10% of the cross-sectional area of the channel feeding that channel, e.g., from about 0.9 to about 1.1 times the area. In preferred aspects, these devices have a channel network comprising at least two or more channel segments in fluid communication with the detection channel. This allows for multiple inlets and optionally, multiple outlets whereby the stagnation zones present in the wider detection channel are removed. As shown in FIG. 7, panel B, two inlet channels 720 and 750 respectively, intersect through-hole 740 leading to the detection channel 710 whereby fluid streams are flowed simultaneously into and out of the detection channel 710 through outlet channels 760 and 730, thereby reducing the "dead" pockets of fluid flow in the detection channel significantly. Alternatively, the stagnant zones may also be removed by providing an inlet 910 and/or outlet channel 920 with a wider cross-section at the point of intersection with the detection channel or through-hole 930 as shown in FIG. 9. Each of these channel configurations facilitate uniform fluid velocity throughout the detection channel and thereby eradicate problems resulting from stagnation zones or dead pockets in that channel.

For the same reasons offered above, it is generally desirable to minimize the volume of the detection channel, while optimizing the detection path length through the detection channels. As such, the detection channel segment will typically have a volume that is less than 100 nl, preferably, less than 10 nl, and more preferably, less than 1 nl.

The systems of the present invention employ planar microfluidic channel networks that typically are fabricated from two or more substrate layers. In general, such planar devices include a first channel or network of channels that is defined between a first and second substrate layer, and contained within a first plane defined by the two substrate layers. In particular, the two or more planar substrates are bonded together on their broad planar surfaces to produce a body that is also planar in structure, and has the channels defined within its interior at the interface of the two or more original substrates. In accordance with the present invention, a detection channel segment is provided that is orthogonal to the first plane and in fluid communication with the first channel or network of channels and is disposed through the second substrate layer, e.g., as a via. In preferred aspects, a second channel or network of channels is disposed between the second substrate layer and a third substrate layer, so that the detection channel segment provides a fluid junction between the first and second channel networks.

Figure 3A:
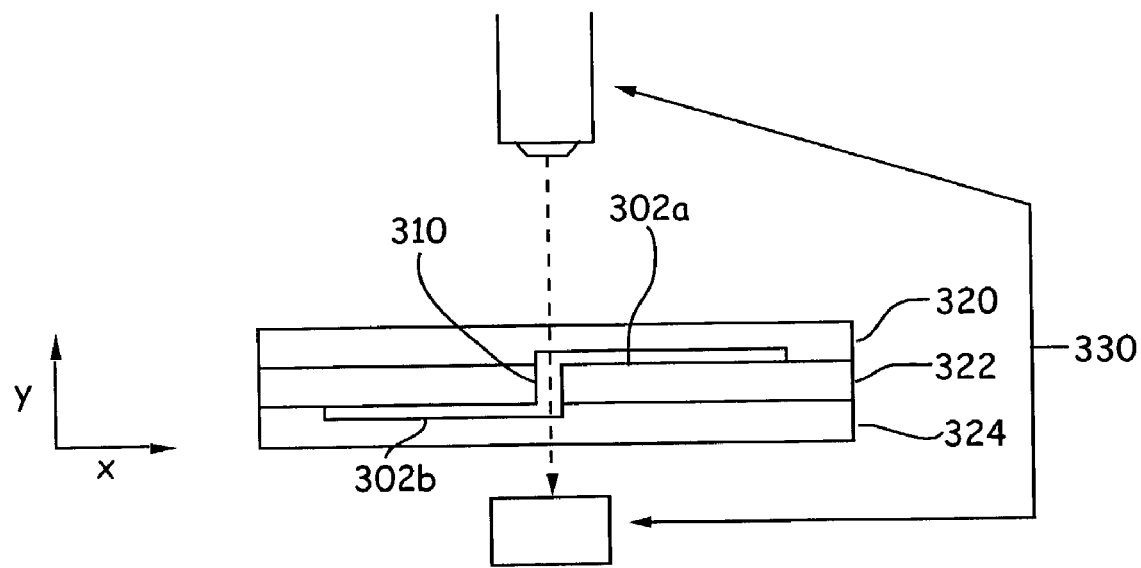
FIGS. 3A and 3B schematically illustrate an alternate exemplary configuration of a microfluidic device and detection system in accordance with the present invention.

A schematic example of a device employing this structure is provided in FIG. 3. As shown in FIG. 3A, a first channel 302a or channel network is disposed between first and second substrates 320 and 322, respectively. A second detection channel segment is provided as a via 310 through the second substrate 322. As shown, this via 310 fluidly communicates with a third channel segment 302b or channel network, which is defined between substrates 322 and 324. As shown the first channel or channel network is fabricated as a groove in the first substrate layer 320, while the third channel network is fabricated into the third substrate layer, with the second substrate layer sealing the grooves to define the respective channels. However, it will be appreciated that in certain preferred aspects, the channels would be fabricated into the middle or second substrate 322, in order that all microfabrication takes place on one single substrate. In particular, one could etch all of the requisite channels or channel networks on opposite sides of a single substrate, and provide a via through that substrate. Sealing the central substrate then involves sandwiching the second substrate between two outer substrate layers, e.g., the first and third substrates.

Figure 8A:
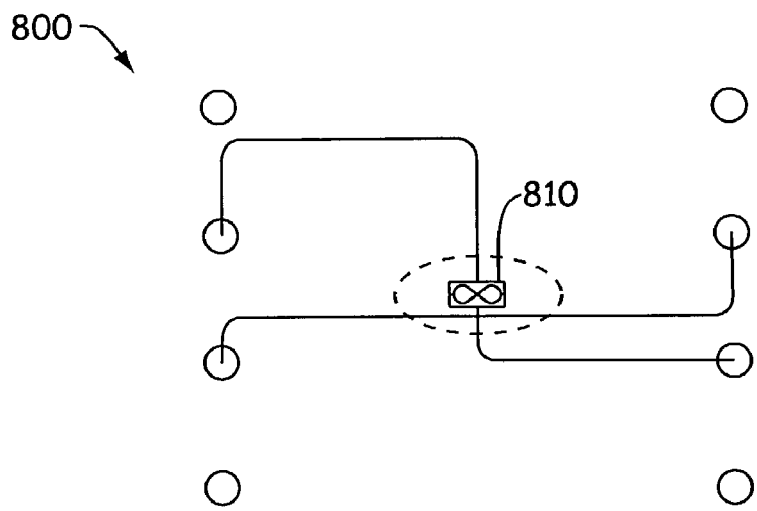
FIG. 8, panels A, B and C illustrates an embodiment of a channel network intersecting an orthogonally situated detection channel in a microfluidic device wherein the rinse time of the detection channel is decreased by flowing multiple streams into the detection channel.
Figure 8B:
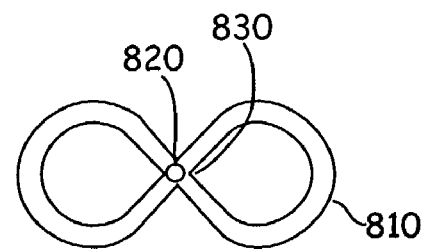
Figure 8C:
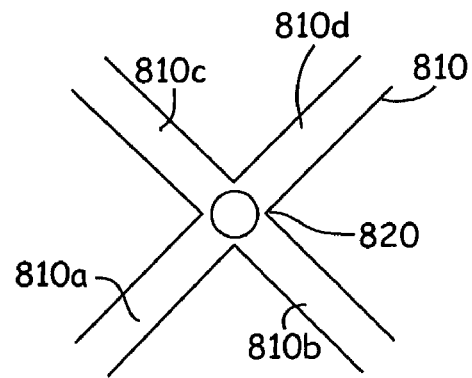

In one embodiment of the device, a first channel network is disposed in the first and second substrates and a second network is disposed between the second and third substrates. A through-hole in the second substrate provides fluid communication between the first and second channel networks. At least two or more channel segments in the first channel network intersect the through hole at a first junction located at a first end of the through-hole. At least two or more channel segments in the second channel network intersect the through-hole at a second junction located at a second end of the through-hole. FIG. 8, panels A, B and C illustrate a typical layout of such a channel structure. Panels A, B and C show a top view of a microfluidic device 800, wherein a first channel network 810 intersects through-hole 820 at a first junction 830. The channel network comprises a "figure 8" layout whereby four channel segments 810a, b, c and d intersect the through-hole 820 at the first junction. This type of channel layout provides for improved fluid flow within the through-hole 820 as discussed above, e.g., helps to reduce dead pockets of fluid flowing through through-hole 820. Also, as noted above, an alternative channel layout for improving the flow pattern in the through-hole comprises providing wider inlet and outlet channels intersecting a through-hole. Such a layout is illustrated in FIG. 9, wherein a wide inlet 910 (and/or outlet 920) is shown to facilitate uniform velocity through a narrow channel region 930.

The channels of the device are fabricated first as grooves in a first planar surface of one of the substrates. Fabrication techniques often depend upon the types of substrates used. For example, silica based substrates are generally fabricated using photolithographic techniques followed by wet chemical etching of the grooves into the surface of the substrate. Polymeric substrates, on the other hand, can have the grooves embossed into the planar substrate surface, or molded into the surface using, e.g., injection molding techniques. Other techniques, such as LIGA techniques, laser ablation techniques, micro-machining techniques and the like are also optionally employed. A second substrate layer is then overlaid and bonded to the first substrate layer to seal the grooves as the enclosed channels of the device. A variety of different channel geometries can be effectively generated using these techniques, in order to accomplish a variety of different operations. Bonding of aggregate substrate layers can be done by any technology useful in such cases, provided the process does not excessively interfere with the structures, e.g., channels, in the interior of the device. Examples of bonding methods include thermal bonding, anodic bonding and bonding by adhesives. Different bonding techniques may be selected based upon desired substrate composition and/or structural tolerances of the finished device.

In accordance with preferred aspects of the invention, the detector is oriented substantially perpendicular to the planar body structure of the device, e.g., as is conventionally done in microfluidics systems. This allows use of conventional instrumentation, e.g., an Agilent 2100 Bioanalyzer, in detecting from the microfluidic devices described herein. In order then to orient the detection channel in the plane parallel to the detection light, the present invention provides channel networks that include detection channel segments that extend out of the plane of the planar device, itself. In particular, such devices include a first channel portion that is in the plane of the overall body structure by virtue of being defined between two planar substrates. A second channel segment, e.g., the detection channel segment, extends out of that plane, e.g., perpendicular to the first channel plane, to provide the channel length along which detection is carried out. In typical preferred aspects, the detection channel segment is defined, at least in part, through one or more of the two planar substrates, e.g., as an aperture through substrate. The detector is then oriented to be directed over the detection channel segment so as to detect along the length of this segment. An example of a microfluidic device having this channel configuration and associated detector is illustrated in FIGS. 3A and 3B from side and perspective views.

Figure 3B:
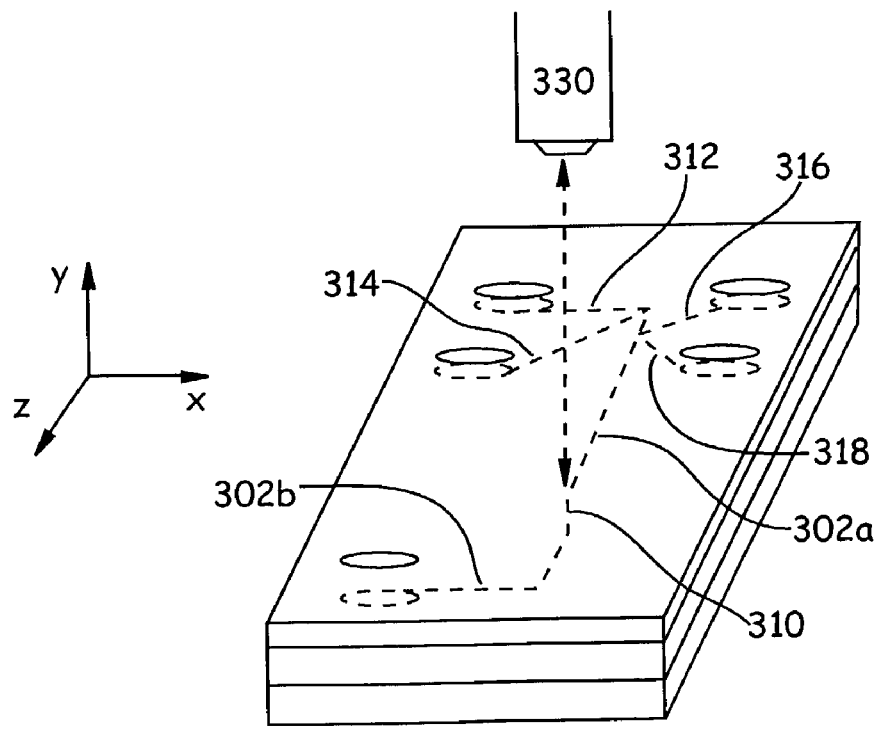

As shown in FIGS. 3A and 3B and described above, a first channel segment 302a is defined between two planar substrates 320 and 322. The first channel segment is in fluid communication with the detection channel segment 310 that extends out of the plane of the first channel segment 302a, e.g., by being disposed through substrate 322. The detector 330 is then oriented to direct and receive light through the entire length of channel segment 310, e.g., by being directed through channel segment 310 from one end. Additional channel segments are optionally provided connected to the other end of the detection channel segment 310. For example, a third channel segment 302b is shown in fluid communication with detection channel segment 310. This additional channel segment 302b is defined between substrate 322 and 324 using, e.g., a multilayer chip configuration. As can be seen in this embodiment, the first and second channel segments 302a and 302b run in or parallel to a first plane, e.g., as shown by the x axis, while the detection channel segment 310 runs in or parallel to a second plane (as shown by the y axis) that is perpendicular to the first plane. The detector 330 is then directed to be parallel with the second plane, e.g., directed along the length of the detection channel segment 310.

Fabrication of the detection channel, e.g., channel segment 310, as a via through one substrate may be carried out by a number of methods. For example, in the case of polymeric substrate, the via may be molded into the substrate. Alternatively, the via may be laser ablated or drilled through polymer substrates. In the case of silica-based substrates, e.g., glass, quartz or silicon, the via may be either drilled or etched through the substrate using similar techniques as used in the fabrication of the channel networks. In certain cases, it may be preferred to employ a silicon substrate as that substrate through which the via is fabricated. Specifically, a monocrystalline substrate allows a straighter etch path through the silicon, as compared to a broadening etch pattern from the isotropic etching of other substrates such as glass and quartz, where etching extends laterally outward from the etched surface, as well as into the etched surface. This permits the etching of an extremely small via through the middle substrate layer, e.g., as small as 10 μm diameter. The semiconductive nature of silicon substrates, however, necessitates the use of an insulating coating, e.g., $SiO_2$, where the device is to be used in an application where electrical currents are applied, e.g., those applications employing electrokinetic movement of materials. In many cases, however, only pressures are employed to move materials and no coating is necessary. Providing insulating coatings on silicon substrates is well known in the art. See, e.g., VLSI Fabrication Principles, Ghandi. In such cases, the use of a silicon intermediate layer and glass or quartz outer layers provides consistent surface properties, e.g., both are $SiO_2$.

In fabricating devices of dissimilar materials, e.g., quartz outer layers and silicon or glass intermediate layers, materials are generally not bonded by conventional thermal bonding. In particular, because silicon or conventional glass, e.g., soda lime, and quartz have significantly different thermal expansion coefficients, thermal bonding is more likely to fail, as the different materials expand differently during the bonding process. Accordingly, where different materials are desired, bonding is generally carried out through non-thermal means, e.g., by adhesive bonding. In particularly preferred aspects, adhesives useful in bonding glass, silicon and quartz are generally commercially available and may vary depending upon a particular application, including, e.g., Optocast 3505-VLV from Electronic Materials Inc, Breckenridge, Co. The adhesive is generally applied by providing additional, typically wider channels between aggregate substrate layers, which channels communicate with an edge of the substrate or an open reservoir in the mated substrate layers, e.g., when the layers are assembled or bonded with water in a nonpermanent fashion, i.e., prior to thermal fusing. Adhesive is then applied to these channels and allowed to wick into the space between the substrate layers. Alternatively, the adhesive is applied to the junction of the aggregate layers, e.g., at the edge, and the adhesive is permitted to wick between the assembled aggregate layers. Alternatively, the adhesive is contact applied, e.g., using a roll or pad, followed by assembly of the aggregate layers of the device.

In operation, the devices and systems of the invention perform one or more analytical operations followed by detection of the results of the one or more operations within the detection channel region. By way of example, and with reference to the device of FIG. 3, reaction components are introduced into channel segment 302a, e.g., from one or more of side channels 312, 314, 316 and 318. The product of a reaction of these reagents is then moved along channel segment 402a and through channel segment 310. Once within channel segment 310, the detector 330 then detects the reaction products, until they move out of the detection channel segment 310 and into channel segment 302b.

As noted above, the systems of the present invention typically employ optical detection schemes, e.g., based upon the absorbance, fluorescence, transmissivity, etc. of the contents in the detection channel segment. In accordance with the present invention, one can use either less sensitive optical detection schemes, e.g., absorbance based systems, or one can gain substantial sensitivity using fluorescent detection. For example, in a number of biochemical analyses, it would be desirable to employ UV absorbance based detection, e.g., to detect the presence of complex chemical structures, i.e., nucleic acids, polypeptides, etc. However, in conventional capillary and microfluidic systems, volumes are too small to detect typical concentrations. In accordance with the present invention, however, the volumes that are subjected to detection are increased, allowing more sensitive detection using these methods. Alternatively, where fluorescent detection methods are employed, increasing the volume of the detected material substantially increases the sensitivity of that detection.

Based upon the foregoing, it will be appreciated that the detector employed in the systems of the invention may include a number of different detector types, including epifluorescent detectors that include a light source, e.g., a laser, laser diode, LED or the like. The light source is directed at the detection channel segment using an appropriate optical train, which also collects fluorescence emitted from the detection channel segment. Examples of fluorescent detectors are well known in the art.

In preferred aspects, an absorbance detector is employed in the systems of the invention. In order to detect the amount of light that is transmitted through the detection channel segment and by subtraction, the amount of light absorbed by the material in the channel, the light source and detector are typically disposed on different sides of the detection channel segment, e.g., a light source disposed above the planar substrate or proximal to one end of the detection channel segment, e.g., as indicated by the detector 220 in FIGS. 2A and B, and the detector 222 disposed below the detection channel or proximal to the other end of the detection channel segment. As used herein, the term proximal does not denote a particular distance but is used to denote relative position, e.g., of the detector components (light source and detector), relative to the detection channel and each other. Again, absorbance based detectors are well known in the art and are readily configured for use in the systems of the present invention. In preferred aspects, such absorbance detectors include light sources that produce light in the UV range of the spectrum, for use in detecting materials of interest, e.g., proteins, nucleic acids, etc.

Figure 4:
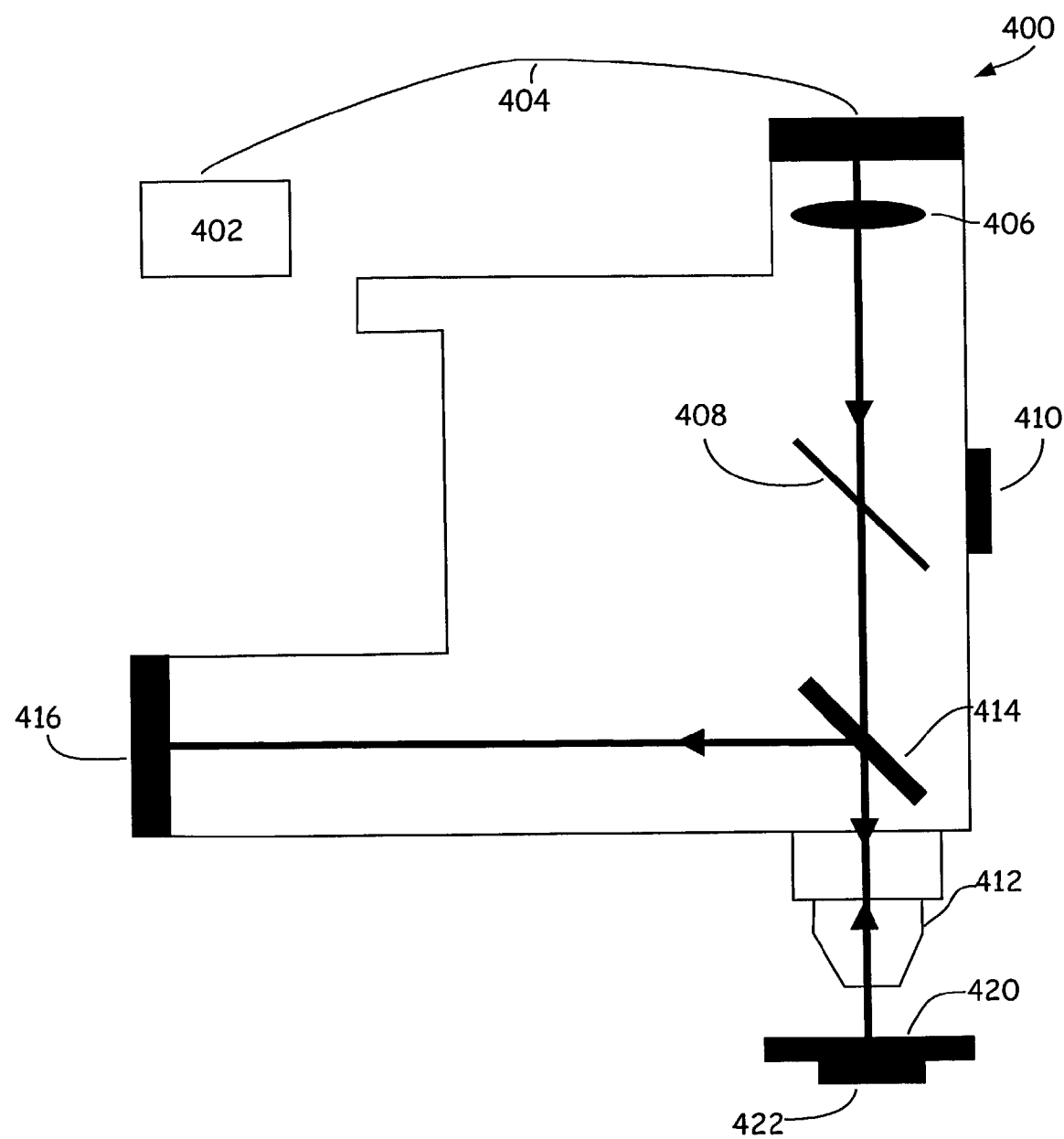
FIG. 4 illustrates an exemplary optical detection system for use in conjunction with the present invention.

An exemplary absorbance detector unit is illustrated in FIG. 4. As illustrated, the detector 400 includes a light source 402. The specific light source is generally selected for broadest application or to provide light that is particularly suited for a given application. This includes arc lamps, lasers, or the like, e.g., mercury arc lamp, deuterium lamp, or the like. As shown, the light from the source 402 is directed into an optical train within the body of the detector 400 via an optical fiber 404. The light then passes through a collimating lens 406. A first beam splitter 408 is provided to divert a portion of the light onto a reference detector 410, while permitting the remainder (typically a substantial percentage, e.g., 95+%) of the light to pass through.

The remainder of the light is directed through an objective lens 412 that focuses the light in the detection channel segment within the microfluidic device 420. That portion of the light that is not absorbed by the sample in the detection channel is then detected by the signal detector 422. Changes in this signal that result from changes in that absorbance of the material flowing through the detection channel are then identified and quantified.

In an optional aspect a second beamsplitter 414 is provided in the optical train which directs a portion of the reflected light signal from the microfluidic device 420 onto a CCD camera 416. This allows the operator to manually position the detector over the detection channel segment in the microfluidic device. In particular, light reflected from the microfluidic device is gathered by the objective lens 412 and directed back to the second beamsplitter 414 and focused onto the CCD camera 416, where the detection channel segment, or an indicator of that channel's location, is imaged. Once the image is observed, the objective 412 is moved to maximize the amount of light striking the detector 422. The objective 412 is then lowered to a desired height offset from the middle of the device 420 where the detection channel is located. Further optimization of positioning is carried out by adjusting the objective in all three dimensions to maximize the amount of light hitting the detector 422. In optional aspects, fluorescence detection elements are optionally or alternately employed in the detection system, e.g., employing an emission filter and a photodiode or PMT in place of the CCD camera shown in the exemplary detector of FIG. 4.

In some cases, it may be desirable to provide a barrier that prevents excess light from being detected by the detector, and thereby reducing the resolution and sensitivity of the system, e.g., by allowing light that has not passed through the sample to impact the detector, thereby giving an inaccurate absorbance reading for the sample. This can be accomplished by placing the device within a light sealed chamber but for access by the detector, e.g., through an aperture over the detection channel segment. Alternatively, the device itself may be provided with a barrier layer that includes an aperture over the detection channel segment. Such layers may include applied layers that are then etched or ablated to provide an aperture over the detection channel segment. Alternatively, a film layer having such an aperture may be overlaid on the surface of the device. These barriers function as spatial filters to filter out scattered light both within and from without the detection channel segment.

In a further alternative, the detection channel segment may be fabricated in a non-transparent substrate, e.g., silicon, in order to cut back on reflected light levels that are detected. Similarly, additional intermediate layers may be provided that accomplish the same goals, e.g., reduce reflected light while providing a small aperture for detection. By way of example, a metal layer may be applied over the detection channel, with a small aperture disposed over the detection channel to permit the passage of light. As with the use of a nontransparent intermediate layer, in order to ensure maximum light directed into and exiting out of the detection channel, it is generally desirable to provide the spatial filter, e.g., the aperture, as close to the detection channel segment as possible, or if possible, provide the detection channel segment as the aperture or transparent region through the intermediate layer. As a result, in preferred aspects, the metal layer is provided on one or both surfaces of the intermediate substrate, and the detection channel itself forms the aperture. One method of fabricating the device of this structure is illustrated in FIG. 5C. As shown, the overall device includes upper, lower and intermediate substrate layers (502, 504 and 506, respectively). A first channel segment or network 508a is provided in one or both of the interfacing surfaces, e.g., the surfaces that face each other and are mated together in the assembled device, of the upper and intermediate substrates so as to define a channel segment or network between the upper substrate and intermediate substrate 504, while a second channel segment or network 508b is fabricated into one or both of the interfacing surfaces of the lower and intermediate substrates, so as to provide a channel segment or network between the lower substrate layer 506 and the intermediate substrate layer 504. Detection channel segment 510 is shown provided through the intermediate substrate layer 504, linking the first channel segment to the second channel segment. As shown in FIG. 5C, a metal surface 520a and 520b is provided on the upper surfaces of the lower and intermediate substrate layers such that the metal layer is positioned in the assembled device to surround the junctions of the detection channel with the first and second channel segments or networks 508a and 508b, respectively. In this case, the sputtered metal is in an "O" shape surrounding the opening of the detection channel segment, and forms a light barrier layer surrounding the opening of the detection channel segment. In order to accommodate the additional material on the surface of the intermediate layer, or optionally, on the upper and lower layers, one can provide a receiving cavity or well 522 and 524 on the opposing substrate to receive the additional material and thus allow voidless bonding of the various layers. The lower layer is illustrated as including an opening 526 for receiving a pipettor element or capillary, e.g., capillary 528 from FIG. 5B.

The metal layer is generally applied by known methods including sputtering methods familiar to those skilled in microfabrication techniques, e.g., sputtering, CVD, etc. while the receiving wells are fabricated by the same methods used to fabricate the channel segments or networks, e.g., wet chemical etching, etc., of silica based substrates or injection molding, embossing or laser ablation, etc., of polymeric substrates. FIG. 5D illustrates the assembled configuration of the device shown in FIG. 5C.

In an exemplary device, the sputtered metal "O" is provided at a thickness of about 0.8 μm where the open center of the layer has an inner diameter (ID) of approximately 80 μm and an outer diameter (OD) of approximately 300 μm. The receiving wells are then provided with comparable or slightly larger dimensions to accommodate the additional sputtered material.

Figure 5A:
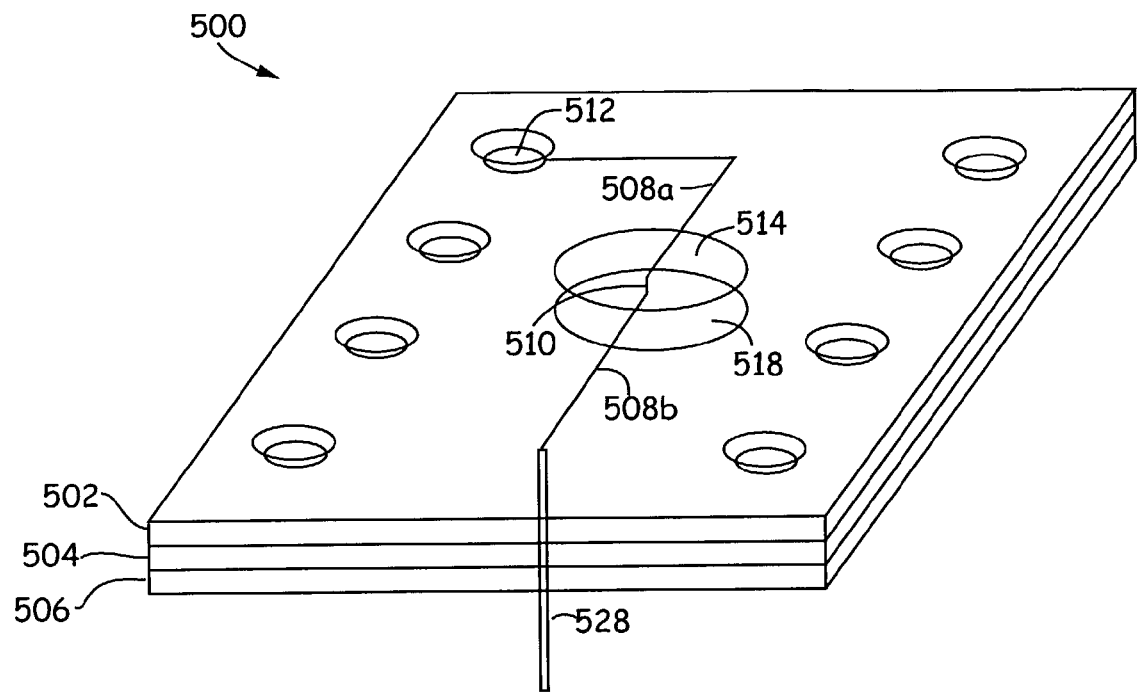
FIG. 5A illustrates a microfluidic device employing a detection channel as envisioned by the present invention. A close-up view of the detection channel segment is provided in FIG. 5B.
Figure 5B:
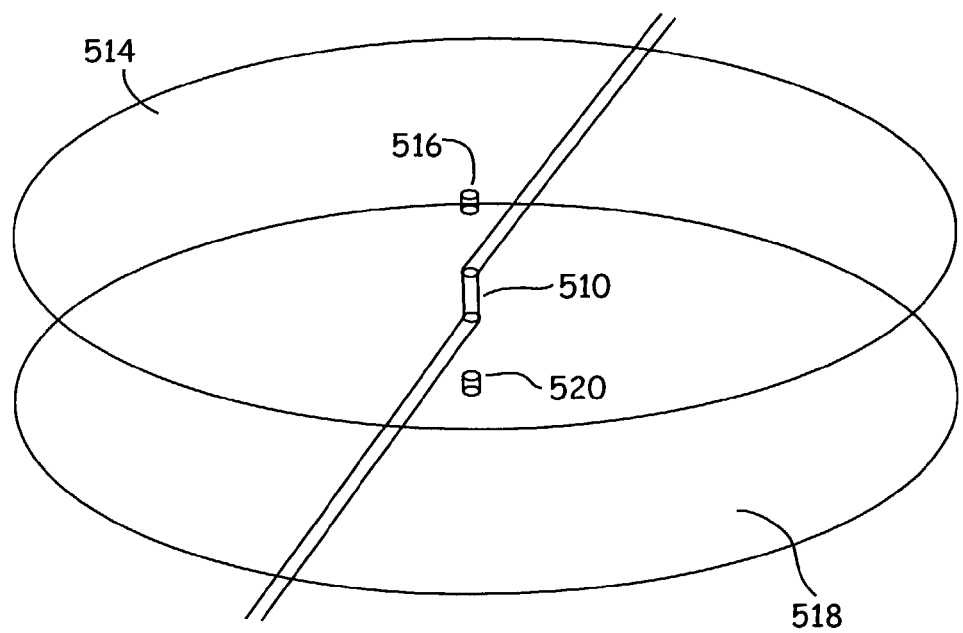
FIGS. 5C and 5D illustrate different views of an alternate configuration of a device having a detection channel in accordance with the present invention.
Figure 5C:
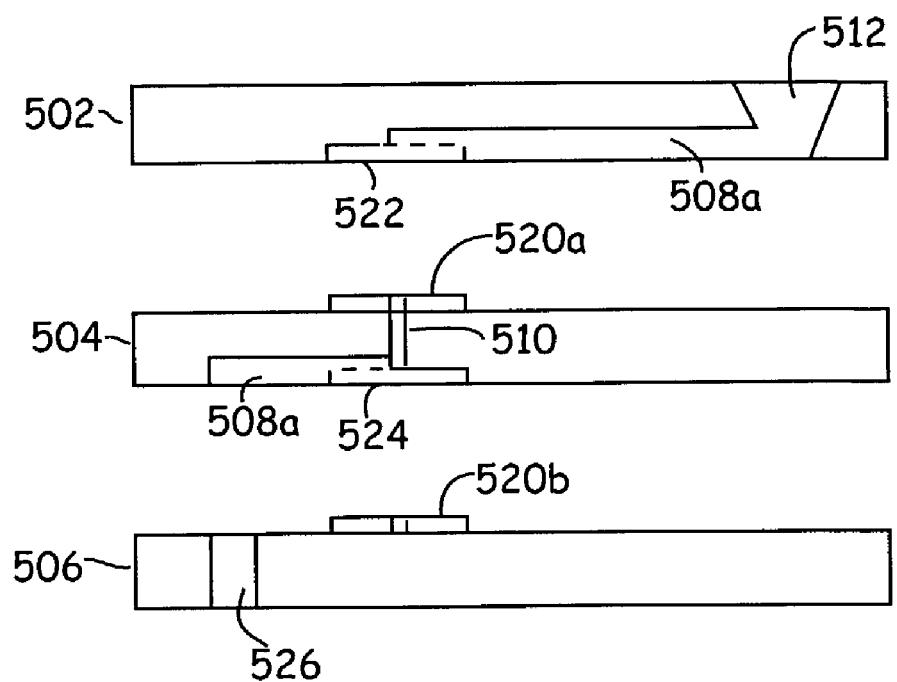
Figure 5D:
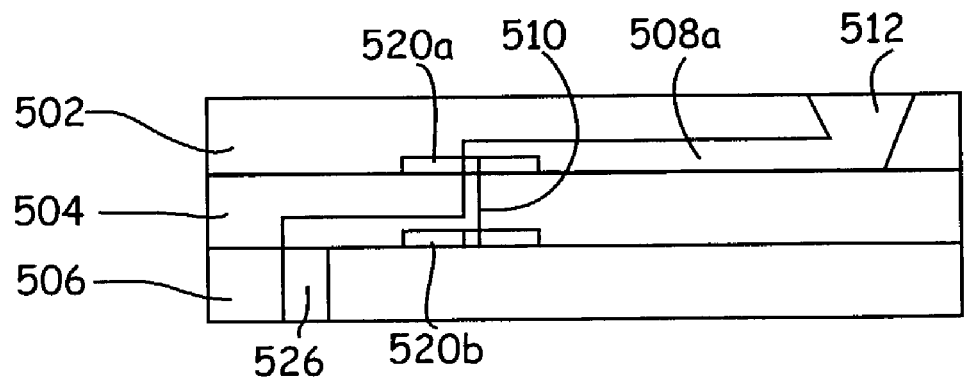

As can be seen from the above-described examples, the spatial filter may be provided on an exterior surface of the completed or assembled body structure, e.g., as shown in FIGS. 5A and B, or it may be provided within the interior region of the assembled body structure, either as an inserted structure, i.e., a metal o-ring, e.g., as shown in FIG. 5C and 5D, or as an aperture in an intermediate opaque layer that is integral to or separate from the substrate through which the via is disposed. The spatial filters on either end are provided either at the ends of the detection channel segment or between the ends of the detection channel segment and the relevant portion of the overall optical detection system, e.g., the light source and/or the optical detector.

As described above, the present invention typically involves an improved configuration of an analytical channel network and the detector used to detect materials within that channel network. Typically, previously described microfluidic systems fill out the remainder of the elements employed in these systems. For example, overall microfluidic systems also typically employ a fluid direction and control system that causes and directs the flow of fluids within the microfluidic channel networks. Such flow control systems are preferably a combination of a pressure controller system, e.g., a pressure or vacuum source applied to one or more ports in the channel network, as well as a channel network configuration that is optimized to yield a particular flow profile under the applied pressure differentials in the system. For example, in some preferred cases, a single vacuum source is applied to one port in a microfluidic channel network. Relative flow rates of materials in all of the various channels is then controlled by the designed flow resistance of the channels of the device. In alternate methods, multiple pressure and/or vacuum sources are applied to a plurality of different ports of the device to regulate pressure differentials across different channels of the device at different times, to control the flow profiles within the device. Such multiport pressure controllers are described in, e.g., PCT Publication 01/63270, and incorporated herein by reference in its entirety for all purposes.

In alternative embodiments, the devices of the invention employ electrokinetic material direction systems. Electrokinetic systems typically operate by applying electric fields through channels in order to cause the movement of materials through those channels. Electrokinetic movement can include one or both of electrophoresis and electroosmosis.

Electrokinetic material direction systems in microfluidic channel networks typically include electrodes placed at the termini of the various channels of the channel network, e.g., at reservoirs or ports disposed at those unintersected termini. Each electrode is then coupled to one or more power supplies that deliver controlled electrical currents through the channels of the device to drive the movement of material either through electrophoresis or electroosmosis. Examples of such systems include the Agilent 2100 Bioanalyzer and associated Caliper LabChip® microfluidic devices. Electrokinetic control of material movement in microfluidic channel networks has been described in detail in, e.g., U.S. Pat. Nos. 5,588,195 and 5,976,336, each of which is incorporated herein by reference for all purposes. Generally, such systems employ pin electrodes that contact fluid filled reservoirs at the termini of the channels, to deliver electrical current through the various channels of the network. By controlling the amount, duration and channels through which current is applied, one can precisely control the direction and velocity of material movement through those channels. Alternatively, electrical circuits are included on the microfluidic device and are interfaced with controllers via one or more slide connectors. These instruments can be readily configured to operate in accordance with the present invention, e.g., by including an improved channel network such as those described herein, interfaced with the controller-detector instrument.

EXAMPLES

Example 1

Efficacy of Orthogonally Oriented Detection Channel Segment

A microfluidic system employing an absorbance detection scheme was assembled employing the detector shown in FIG. 4. In addition, the system employed a simple microfluidic device having the structure illustrated in FIGS. 5A and 5B. In particular, the device 500 was fabricated as an aggregate of three substrate layers 502, 504 and 506, where channel 508a was fabricated between substrates 502 and 504 while channel 508b was fabricated between substrates 504 and 506. The two channels were connected by a via 510 fabricated through substrate layer 504, that forms the detection channel segment. The via or detection channel segment 510 was disposed through the entire center substrate that had a nominal thickness of 700 µm. When added to the depth of the channels on either end, this yielded a detection path length of approximately 720 µm Channel 508a terminated at one end at reservoir 512, and at the other at via 510, while channel 508b terminated at one end at via 510 and at the other end at a sampling capillary 528. In order to ensure that the only detected light was that which had passed through the detection channel, metal disks 514 and 518 were placed over the surfaces of the device surrounding the detection channel segment. The disks included small apertures (50 µm) 516 and 520, respectively, that were positioned over the detection channel segment or via 510.

The detector was positioned as described above, with the signal detector placed below the device, e.g., below aperture 520. Specifically, the objective lens was positioned over the aperture 516 such that light from the light source was directed through the aperture and the detection channel segment and that aperture was imaged on the CCD. The Objective was then lowered by a distance equal to the offset in height between the aperture and the middle of the detection volume. The position was fine tuned by adjusting the position of the detector in all three dimensions to maximize the light that was incident on the detector.

The sampling capillary 528 was used to draw sample materials into channel 508b. This involved application of a negative pressure at reservoir 512 to sip sample materials from sample wells or tubes. After being drawn into channel 508b, the material moved into the detection channel segment 510 at which point it was subject to detection. The material then moved into channel 508a and out toward reservoir 512.

Figure 6:
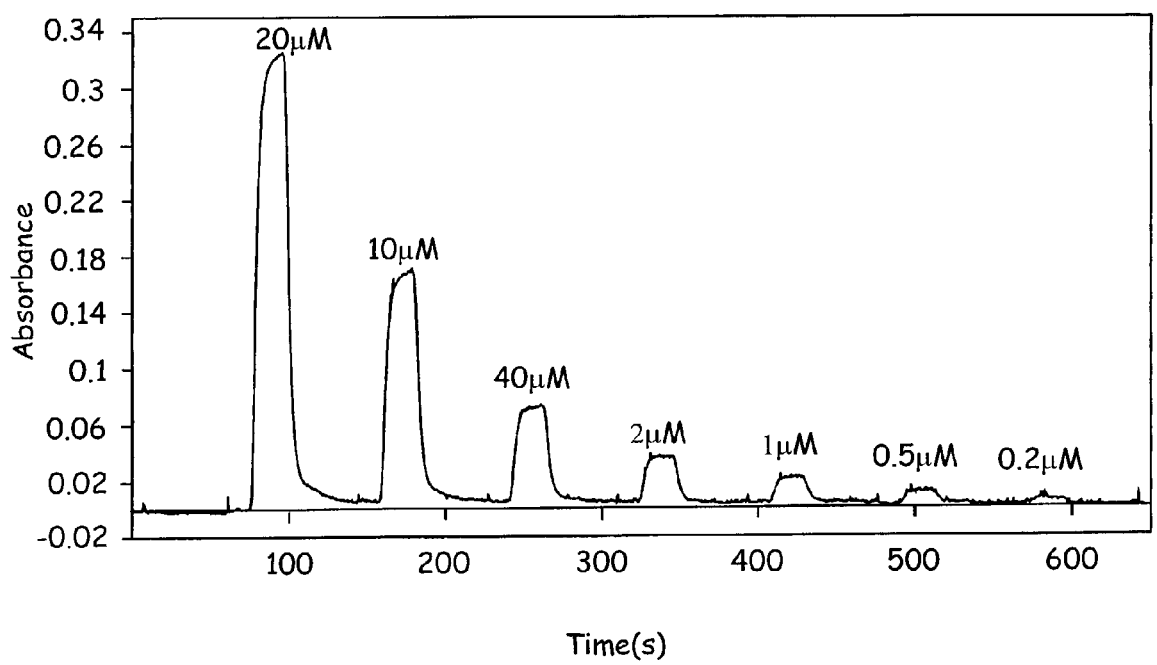
FIG. 6 is a plot of absorbance of a sample material passing through a detection channel segment.

Sample plugs of 25 mer DNA were sipped into the chip through the capillary element and moved into the detection channel segment. Successive plugs were introduced at regular intervals that contained diminishing concentrations of the 25 mer (20 µM, 10 µM, 4 µM, 2 µM, 1 µM, 0.5 µM and 0.2 µM). The plot absorbance is shown in FIG. 6. As can be seen, one can readily distinguish concentration differences from the absorbance of the different sample plugs, as detected in the system of the invention.

Comparative measurements were made of one sample material in the 720 µm long detection channel segment, as described above, and at a 1/72 concentration in a conventional detection orientation, e.g., detection path length of 10 µm, that was the depth of the channel. A measurement of 250 µM solution in the 10 µm deep channel allowed 86% (absorbance=0.061) of the light to hit the detector, while a 250/72=3.5 µM solution of the 25 mer traveling through the 720 µm through hole allowed 87% (absorbance=0.065) of the light to pass through the sample. As can be seen, these measurements are roughly equivalent, indicating the efficacy of the present invention in measuring absorbance in relatively dilute sample materials.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A microfluidic device, comprising:
   a body structure comprising at least first, second and third planar substrate layers mated together;
   a first channel network disposed between the first and second substrate layers, said first channel network comprising at least first, second, third, and fourth channel segments in the same plane;
   a second channel network disposed between the second and third substrate layers;
   at least a first channel providing fluid communication between the first and second channel networks, each of said first, second, third, and fourth channel segments of said first channel network being individually fluidly coupled to said first channel whereby at least two fluid streams may be simultaneously flowed into said first channel from said first channel network.

2. The device of claim 1, wherein the at least two fluid streams flowing into said first channel reduce stagnant fluid flow within said first channel.

3. The device of claim 1 wherein said first channel network has a figure 8 configuration.

4. The device of claim 1, wherein said first, second, third, and fourth channel segments of the first channel network have a wider cross-sectional diameter than a cross-sectional diameter of the first channel.

5. The device of claim 1 wherein the first channel is located orthogonal to said first, second, third, and fourth channel networks.

* * * * *